(12) United States Patent
Fua et al.

(10) Patent No.: US 8,588,509 B1
(45) Date of Patent: Nov. 19, 2013

(54) EFFICIENT SCANNING FOR EM BASED TARGET LOCALIZATION

(75) Inventors: Pascal Fua, Vaux-Sur-Morges (CH); Graham Knott, Bougy-Villars (CH); Raphael Sznitman, Zurich (CH); Aurelien Lucchi, Renens (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 30 days.

(21) Appl. No.: 13/535,497

(22) Filed: Jun. 28, 2012

(51) Int. Cl.
*G06K 9/00* (2006.01)
(52) U.S. Cl.
CPC .......................................... *G06K 9/00* (2013.01)
USPC .......................................... 382/144; 382/145
(58) Field of Classification Search
USPC .................................................. 382/144, 145
See application file for complete search history.

(56) References Cited

U.S. PATENT DOCUMENTS

| 8,139,843 B2 * | 3/2012 | Kulkarni et al. ............... 382/144 |
| 2006/0097158 A1 | 5/2006 | Yamaguchi et al. |
| 2008/0056559 A1 | 3/2008 | Hiroi et al. |

FOREIGN PATENT DOCUMENTS

JP    2003331768 A    11/2003

\* cited by examiner

*Primary Examiner* — Kiet T Nguyen
(74) *Attorney, Agent, or Firm* — Blank Rome LLP

(57) ABSTRACT

We presented an approach for speeding-up image acquisition when tasked with localizing specific structures in FIB-SEM imagery. It exploits the fact that low-quality images can be acquired faster than higher-quality ones and yet be sufficient for inference purposes. We have demonstrated greater than five-fold speed-ups at very little loss in accuracy in the context of mitochondria and synapse detection. Furthermore, the algorithm we propose is generic and applicable to many imaging modalities that allow trading quality for speed.

7 Claims, 4 Drawing Sheets

Original    Reconstructed
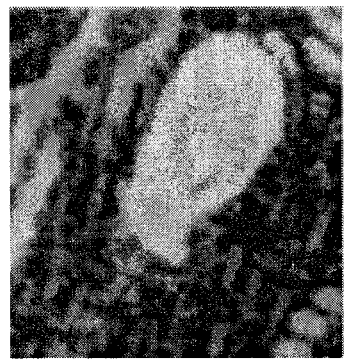 
C=44
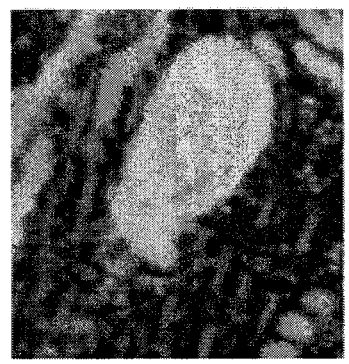 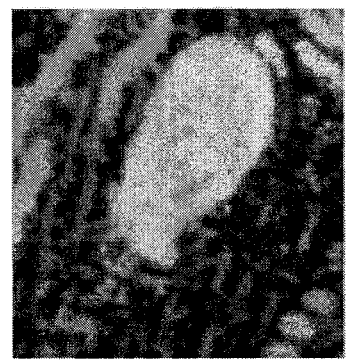
C=12
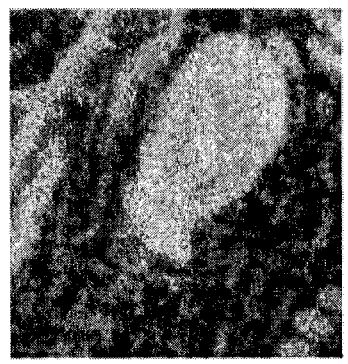 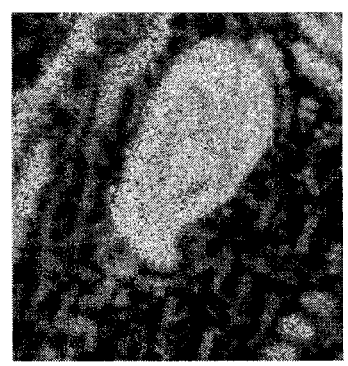
C=4
Fig. 2a
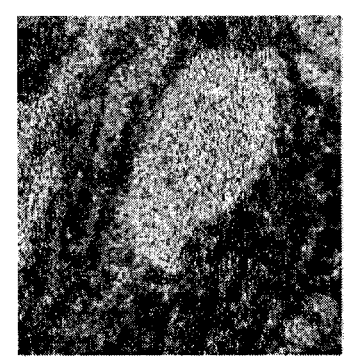 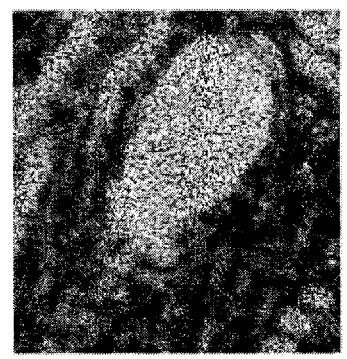
C=1

EFFICIENT SCANNING FOR EM BASED TARGET LOCALIZATION

FIELD OF THE INVENTION

The present invention concerns, in embodiments, an image processing and acquisition method to capture microscopic images, in particular, but not exclusively, layered or three-dimensional images acquired with Focused Ion Beam Scanning Electron Microscope (FIB-SEB) apparatuses.

DESCRIPTION OF RELATED ART

Focused Ion Beam Scanning Electron Microscopes (FIB-SEM) and their ability to image with isotropic resolution of up to 4 nm per pixel are becoming invaluable tools in the study of ultramicroscopic samples, for example the investigation of cell ultrastructure and model organelles, such as mitochondria, synapses, and vesicles, but the technique is not limited to cellular or biologic samples and materials. Acquiring such images involves a painstaking cycle of milling a few nm from the surface of a tissue block using a gallium ion beam or another suitable beam milling technique, scanning each line of a rectangular region of the block face several times, averaging the results until an image of sufficient quality is obtained, milling again, and repeating.

The resulting images have already yielded many new insights in the structure and functioning of cells, but the acquisition process is desperately slow. For example, a typical imaging time of a 10×10×10 µm³ tissue block at full resolution is of about 50 hours. Such lengthy processing times are limiting because neuroscientists now require larger volumes to enable multiple cells, and even entire tissue samples, to be analyzed, which would currently be prohibitively slow. Furthermore, consistent imaging requires considerable precision and dimensional stability along the acquisition time, but thermal changes and other effects can cause the block faces to drift slowly and produce misaligned image series as the acquisition time lengthens, limiting the practical size of the images that can be captured.

A pressing need exists to reduce scanning time without compromising the usefulness of the resulting images.

It has been proposed that Sparse Sampling techniques could potentially lead to a reduction of FIB-SEM image acquisition. The current generation of microscopes, however, cannot perform the required random sampling because imaging extremely small and random locations on the block face would be prohibitively time consuming.

SEM Microscopes with the ability to recognize to some extent images, or portions thereof, matching a predetermined pattern are known in the art, for example by documents US2008056559, US2006097158, JP2003331768.

BRIEF SUMMARY OF THE INVENTION

According to the invention, these aims are achieved by means of

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Figure 1:
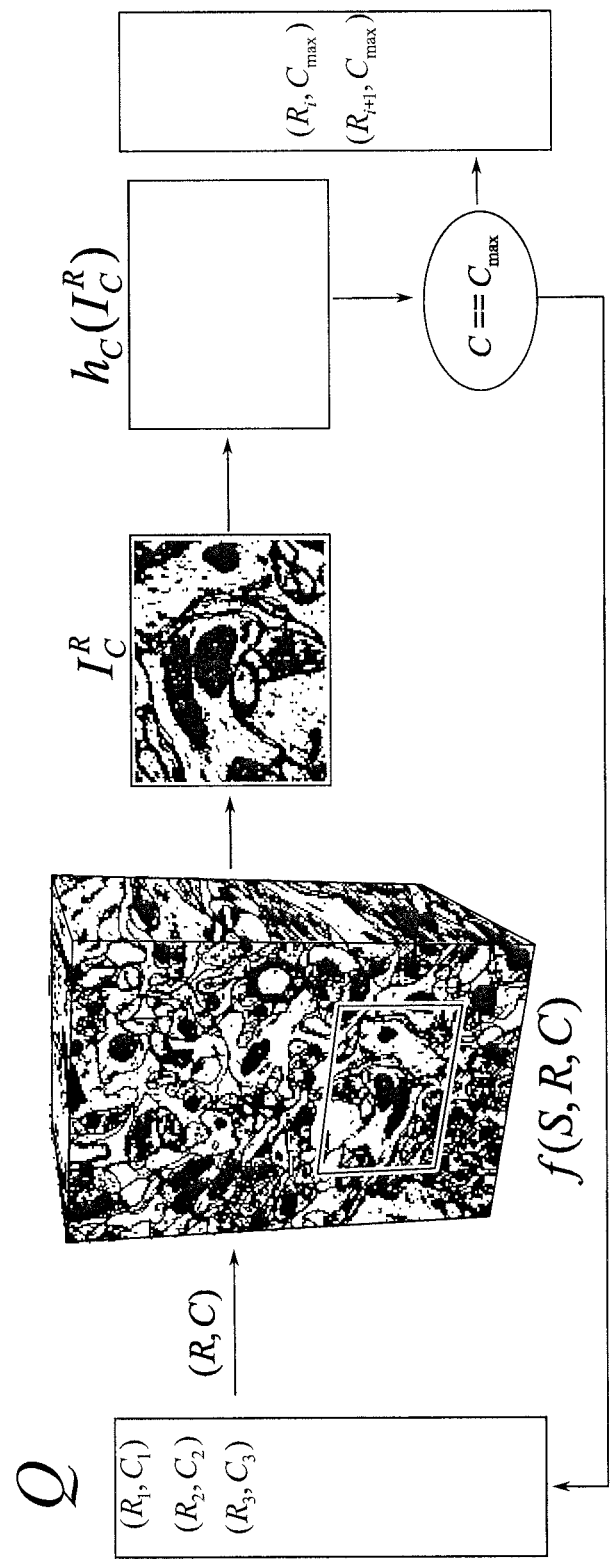
FIG. 1 illustrates graphically and schematically an embodiment of the method of the invention FIG. 2a compares low-scan count SEM images with the simulated images used in the proposed example

The present invention proposes a novel approach to achieving much faster scanning in FIB-SEM microscopes when the images are intended for automated detection, counting, and modeling of predetermined patterns. The inventive strategy involves scanning each image line of the block surface once, or a limited number of times, instead of several times, finding rectangular regions of interest in which target structures might be located, scanning these regions once again, and iterating the process until only relevant regions of the block face have been scanned repeatedly. This process results in much reduced imaging time at almost no performance loss.

The invention stems from the realization that, if it is desired to count or model element matching a predefined patterns that occupy only a small fraction of a sample, precisely imaging the entire volume is a waste of time. The inventive method aims at optimizing the acquisition time while keeping the limitations of microscopes into account, in particular:

Current microscopes are good at scanning rectangular regions. In contrast, microscopes that can quickly and randomly access specific image locations are likely to remain beyond the state-of-the-art for the foreseeable future, thus limiting the usefulness of conventional Sparse Sampling techniques.

Microscopes are optimized to scan lines at one particular speed. Total scanning time and image quality are controlled by the number of times each line of the rectangular regions of interest is scanned. Typically, the final result is the average of these scans. The method of the invention, also indicated as Sequential Region Cascades (SRC) approach, attempts to accelerate the scanning process by optimizing the number of averaged scans, dependent from the likelihood that a region contains a determined structure of interest.

The following description of an embodiment of the invention refers, to fix the ideas to the scanning of a biologic sample and the mapping of organelles, for example mitochondria, or other intracellular structures. The invention is however not limited to such application and can be used to image any kind of microscopic sample.

Contrary to other cascade systems which increase classification accuracy over levels, in the present invention, classification is instead performed on images acquired with varying scan counts. According to an important aspect of the invention, the sample is scanned in successive slices and, once a feature has been found in one slice, it will be seen with very high probability at similar locations in subsequent slices. In a preferred variant, targets that are identified using information locations from previous slices are directly imaged with a larger number of scans, preferably with the largest possible numbers of scans, than the regions in the remainder of the slice. New targets are searched for in the remainder of the slice using the cascade approach.

Let the volume to image be denoted by $V = \{S^1, \ldots, S^T\}$, where $S^t$ corresponds to a slice of the volume. When using a scanning EM microscope, we consider two sets of parameters when acquiring images. First, we define a rectangular region to scan, $R = (r_1, r_2)$, where $r_1$ and $r_2$ are the upper left and bottom right pixel coordinates, respectively. Second, the scan count is defined as the number of times the electron beam images one pixel and denote this value as $C = \{1, \ldots, C_{max}\}$.

Given these two parameters, (R,C), the process of acquiring an image by scanning a region of a slice can be described by the function $f$, where $f:S \times R \times C \mapsto I$. That is, evaluating the function $f(S,R,C)$ provides an image $I^{Rc}$ of size R and corresponds to the average of C independently scanned samples. Typically, the time cost associated with evaluating $f(S,R,C)$ is $C \times area(R)$.

According to an aspect of the invention, the images are analyzed by one classifier or a family of classifiers, $\mathcal{H} = \{h_1, \ldots, h_{C_{max}}\}$. The classifiers are functions acting on images contained in the image space $I_C^R$ and returning values dependent on whether the classifier estimates that a pixel in $I_C^R$ belongs to a determined target structure or not. In the following examples the classifiers $h_c: I_C^R \mapsto \{0,1\}^R$ are binary-valued functions that return 1 or 0 dependent on whether the classifier estimates that a pixel in $I_C^R$ belongs to a determined target structure or not. Other possibilities are however available. Classifiers can be realized in different manners, according to the nature of the targeted structures. Images acquired using different scan counts exhibit different statistics and optionally the invention may use different classifiers trained or optimized to these specific statistics.

Finally, let $P^t$ to be the set of pixels corresponding to the location of target structures in a slice $S^t$. The goal of the inventive method is to discover these sets $\{P^t\}_{t=1}^{t=T}$ for all slices as efficiently and as quickly as possible.

An outline of the algorithm is shown in table 1 and FIG. 1. To begin, the user provides the set of classifiers and the volume to image, $\mathcal{H} = \{h_1, \ldots, h_{C_{max}}\}$ and $\mathcal{V} = \{S^1, \ldots, S^T\}$, respectively. The algorithm begins by forming two data structures that will maintain tuples of regions and scan counts, i.e. (R,C). The first, $\mathcal{P}$, maintains a set of regions deemed the target structure on a given slice. The second, $\mathcal{Q}$, maintains an intermediary list of candidate regions that appear likely to contain target structures within them. Initially, both queues are empty.

Preferably, the method of the invention foresees also the definition of a scan count sequence $Cs=\{C_1, \ldots, C_{max}\}$ determining the possible number of scan that are averaged for each considered candidate region, as it will be discussed in the following. If, for example the scan sequence is set to $Cs=\{1,6,12,44\}$, each candidate region is scanned first one time and then again, dependent from the classifiers' output, to a total 6, 12, 44 averaged scans, until the regions with $Cs=44$ satisfying the classifier are moved into the target list $\mathcal{P}$. As already mentioned, for each scan count the algorithm can optionally provide a specific classifier, trained for the statistics specific to that scan count.

For each new slice, we begin by pushing the entire observable domain as a candidate region using the smallest scan count. The following sequence of steps is then looped, which is called the refining stage and is depicted by FIG. 1. A candidate region and scan count index from the queue $\mathcal{Q}$ is retrieved. The associated image region, $I_C^R$, is then acquired and the corresponding classifier is evaluated by computing $h_c(I_C^R)$. At this point, the binary classification image is searched for disjoint sets of rectangular regions that indicate potential target locations. If newly extracted regions were acquired using the highest possible scan count, these are pushed into the target region queue, $\mathcal{P}$, otherwise, they are pushed into the candidate region queue, $\mathcal{Q}$.. This process iterates until no candidate region remains.

TABLE 1 pseudocode example of the inventive method

Require: Classifiers H = $\{h_1, \ldots, h_{C_{max}}\}$, Volume V = $\{S^1, \ldots, S^T\}$.
Ensure: Regions P are target locations.

TABLE 1-continued pseudocode example of the inventive method

```
P ← empty queue, Q ← empty queue.
for t = 1, . . . , T
    Push ( ([0,0], [M,N]), 1) into Q
    RemoveOverlaps (Q, P)
    while | Q |> 0
        [R, C] ← Top (Q)
        I_C^R ← f (S^t, R, C)
        R ← ExtractRegions (h_C (I_C^R))
        if      C_max == C
                Push(R, C) into P
        else
                Push (R, C +1) into Q
        end if
    end while
end for
```

In addition, before starting the refining stage, the overlapping region that coexists in both $\mathcal{Q}$ and $\mathcal{P}$ are removed. This effectively creates a new set of regions in $\mathcal{Q}$ that are disjoint of $\mathcal{P}$ and reduces the direct need for searching targets likely to have stayed in the same location. Obviously, during the first slice of the tissue block, this step is irrelevant because $\mathcal{P}$ is empty.

FIG. 1 illustrates graphically and schematically an embodiment of the method of the invention. For any slice, the queue $\mathcal{Q}$ contains a list of tuples (R, C) that specify a region and scan count with which the microscope should image. Once an image region acquired, $I_C^R$, a dedicated classifier $h_c$ assigns a binary label to each location in the image for the presence of targets. New tuples are then formed and inserted into $\mathcal{Q}$ or into the permanent queue $\mathcal{P}$.

Examples of Application of the Inventive Method

We used a Zeiss NVision40 FIB-SEM microscope to mill and scan a rodent brain sample of $10 \times 10 \times 1$ μm, which produced 165, $1024 \times 1536$ images. We also collected a second stack of 377, $655 \times 429$ images. In both cases, each line was scanned $C_{max}=44$ times. This took 5 and 12 hours, respectively. We evaluated our algorithm for the tasks of localizing two types of organelle: mitochondria and synapses. Here, we show how the SRC strategy could be used to divide the scanning time by a factor of 10 to 15 depending on the target type.

Test Data:

To demonstrate the validity of the method without modifications to the scanning engine of the microscope, we started from the averaged images at $C=C_{max}$ and synthesized the scans we would have gotten using values of $C<C_{max}$ by appropriately degrading the higher-quality ones. This simulation is believed to provide the same results as a real-time implementation of the method. To ensure realism we proceeded as follows.

Figure 2B:
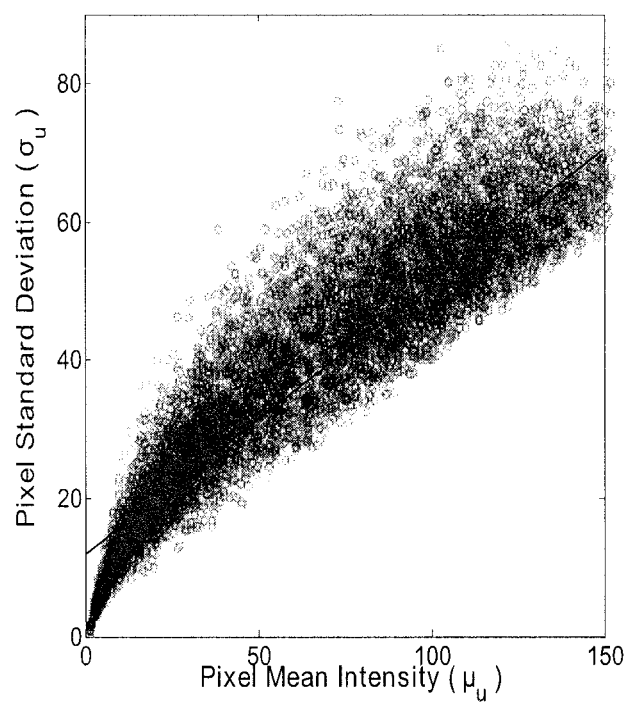
FIG. 2b illustrates the statistics of scanned SEM images FIG. 3 Illustrates the regions scanned by our invention.

Before scanning, and thus destroying, the whole first block, we collected six independent images $\{I_1, \ldots, I_6\}$ of the first slice using a single scanning pass for each and a single one, which we denote as $\hat{I}$, using 6 passes. From this, we first verified that for any pixel location $u$, the gray-level $I_i(u)$ in any of the 6 single-scan images is well approximated by a Gaussian of mean $\hat{I}(u)$ and standard deviation $\sigma_u = m\hat{I}(u)+b$, where m and b are linear regression parameters, as illustrated by FIG. 2*b* where we plot $\mu_u$ against $\sigma_u$ for 10,000 randomly selected pixels. In other words, the gray level variance is directly proportional to the gray level value.

From this, using an image acquired with a large number of scans, we can simulate acquiring an image from a smaller number of scans. For example, a pixel with n scans can be reconstructed by sampling the Gaussian $\mathcal{G}(\hat{I}(u),m\hat{I}($ $u$)+b)n times and averaging the samples. FIG. 2a shows the original (left column) and reconstructed (right column) images using this process with 1, 4, 12 and 44 scan counts.

Experimental Setup:

We tested four scan count sequences—Cs={12,44}, Cs={6,12,44}, Cs={1,6,12,44}, Cs={1,4,6,44}—for synapse and mitochondria detection purposes. In all cases we constructed the classifiers $h_c$ as follows: first we extracted regularly spaced superpixels from model images, from which we computed both intensity histograms and steerable features. We then used 15 training images for each scan count C to train a different Support Vector Machine (SVM) classifier with a Radial Basis Function (RBF) kernel. In the $C=C_{max}$ case, we used the original images and for all other $C<C_{max}$, we used synthesized images obtained as discussed above. The Use of superpixels and Support Vector Machine classifiers for segmenting and recognizing irregular structures is known, and, while desirable, is not an essential feature of the invention, that could also use other classifiers, based on known segmentation algorithms.

An account of the segmentation algorithm used in the following example can be found in Aurélien Lucchi, Kevin Smith, Radhakrishna Achanta, Vincet Lepetit and Pascal Fua, "A fully Automated Approach to Segmentation of Irregularly Shaped Cellular Structures in EM Images" published in the proceedings of the 13$^{th}$ MICCAI Conference, Beijing, DOI: 10.1007/978-3-642-15745-5, pages 463-471, that is hereby incorporated by reference.

Figure 3:
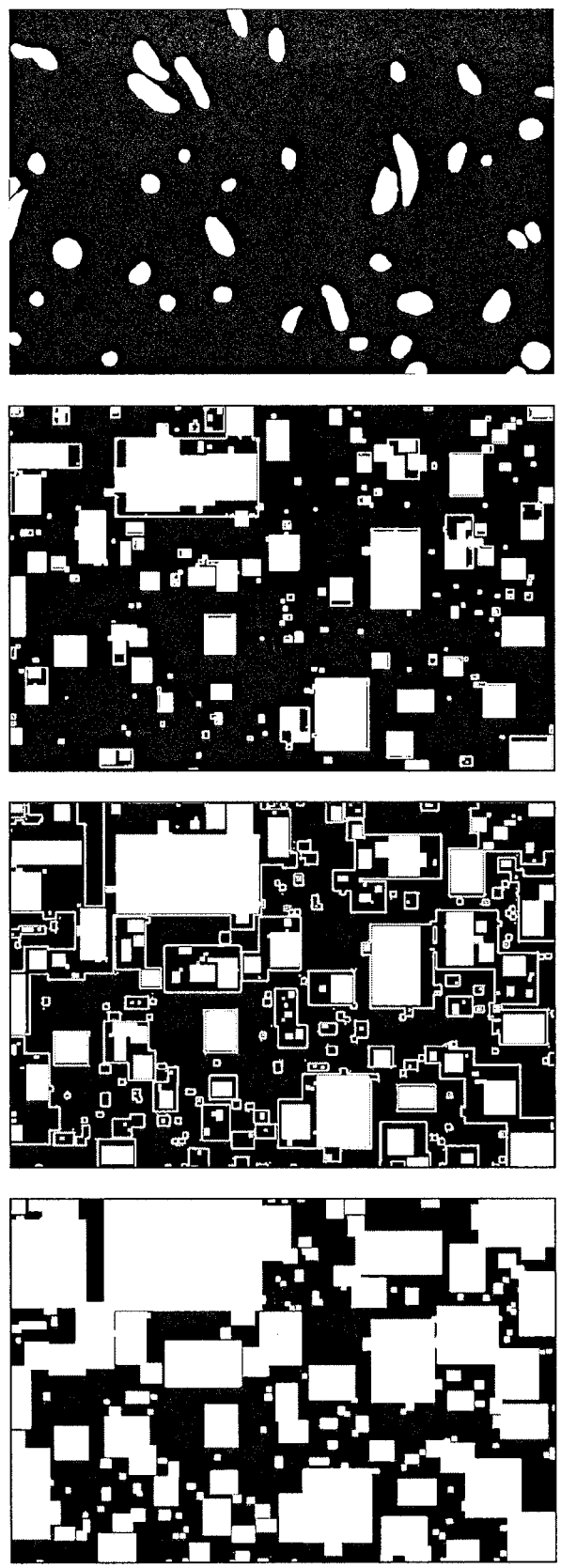

FIG. 3 depicts the algorithm's behavior when attempting to locate mitochondria using the scan sequence Cs={6,12,44}. From left to right, we show the complete set of regions evaluated with each scan count on the initial slice, $S^1$. The white areas in the leftmost image are the candidates at C=6 as white; In the second image, the C=6 candidates are represented as outlines, and the C=12 candidates as white rectangles, while the third images shows as outlines the candidates C=12 and as white areas those for C=44. The rightmost image shows the ground truth regions.

Evaluation:

A goal of the invention is to image with high signal-to-noise ratio all the regions containing target structures-mitochondria and synapses in our experiments—while spending as little time as possible scanning the block faces. In this context, the proper measure of success is the True Positive Rate (TPR) as a function of scanning time, which is what we tabulate in Table 2. The false positive rate is less relevant as false positives only cause irrelevant parts of the block being scanned, which implies no loss of information but a time penalty that the increased scanning time already reflects.

For the purpose of this evaluation, we consider the time cost of one imaging strategy to be the sum of the number of times each individual pixel is scanned. For simplicity's sake, we normalize these numbers by the corresponding count when scanning the whole block at the maximum scan count. As a result, the times that appear in Table 2 are numbers between 0 and 1. The associated standard errors for time and TPR (with a factor of $10^{-5}$ for time scores, and $10^{-3}$ for TPR) are shown in brackets.

From these results, we can see all the scan count sequences we tested provide a significant speed increase, mostly at a very small loss in TPR. By choosing the appropriate sequence we can establish more than five-fold speedups for an insignificant TPR loss. In practice, this means a neuro-scientist could examine and gather statistics for five times as many synapses in the same scanning time.

Note that the choice of which specific scan count sequence to use implies training different classifiers for each scan count value, some of which might be more appropriate than others. For example, the {1,4,6,44} sequence appears to outperform the {1,6,12,44} one, which may imply that additional research into optimizing these sequences might lead to further gains.

The present invention offers a clear reduction of the acquisition time over conventional scanning methods. Targets that cover smaller surface areas, such as synapses (roughly 0.05% of the surface) allow higher time gains then for mitochondria (3 to 5% surface covered).

TABLE 2 acquisition times and true positive rates (TPR)

| Method | Mitochondria | | Synapses | |
| --- | --- | --- | --- | --- |
| | Time | TPR | Time | TPR |
| reference | 1.00 (0) | .989 (2) | 1.00 (0) | .927 (8) |
| SRC: {12, 44} | 0.55 (6) | .982 (2) | 0.43 (5) | .925 (7) |
| SRC: {6, 12, 44} | 0.27 (4) | .969 (3) | 0.18 (3) | .905 (9) |
| SRC: {1, 6, 12, 44} | 0.17 (3) | .945 (3) | 0.09 (2) | .837 (1.1) |
| SRC: {1, 4, 6, 44} | 0.14 (3) | .945 (3) | 0.07 (2) | .853 (1.0) |

The invention claimed is:

1. A method of data acquisition for an apparatus having a Scanning Electron Microscope (SEM) for microscopic imaging and a Focused Ion Beam (FIB) unit for sample milling, the method comprising:
    scanning a sample with the SEM to obtain an image region ($I_C^R$);
    analyzing the image region with a classifier function ($h_i$) that operates on the image region and returns a classification image whose content depends on whether the classifier estimates that a pixel in the image region belongs to a determined target structure or not;
    searching in the classification image for disjoint regions that indicate potential target locations and adding the regions so found to a list of candidates;
    iterating the steps of scanning, analyzing and searching on the members of the list of candidates.

2. The method of claim 1, comprising moving a region from the list of candidates to a list of found targets dependent on predetermined criteria.

3. The method of claim 2, comprising keeping a count of the number of times that a region in the list of candidates is scanned, and wherein regions are moved from the list of candidates to the list of found targets when their scan count exceeds a predetermined value.

4. The method of claim 2, comprising removing overlapping regions existing in both the list of candidates and the list of found targets from the list of candidates.

5. The method of claim 1, further comprising milling a new slice of the sample once the list of candidates is empty, and repeating said scanning, analyzing, searching, and iterating on the new slice.

6. The method of claim 5, comprising imaging directly with multiple scans regions in the new slice that correspond to found targets in a previous slice.

7. The method of claim 1, comprising defining a scan count sequence (Cs={$C_1$, . . . , $C_{max}$}) determining the possible number of scan that are averaged for each considered candidate.

* * * * *